(12) United States Patent
Oka et al.

(10) Patent No.: US 9,915,443 B2
(45) Date of Patent: Mar. 13, 2018

(54) HEATING ELEMENT AND HEATING IMPLEMENT CONTAINING THE SAME

(71) Applicant: KAO CORPORATION, Tokyo (JP)

(72) Inventors: Takeshi Oka, Funabashi (JP); Shouko Senda, Ichikai-machi (JP)

(73) Assignee: KAO CORPORATION, Tokyo (JP)

( * ) Notice: Subject to any disclaimer, the term of this patent is extended or adjusted under 35 U.S.C. 154(b) by 555 days.

(21) Appl. No.: 14/405,943

(22) PCT Filed: Jun. 7, 2013

(86) PCT No.: PCT/JP2013/065821
§ 371 (c)(1),
(2) Date: Dec. 5, 2014

(87) PCT Pub. No.: WO2013/183757
PCT Pub. Date: Dec. 12, 2013

(65) Prior Publication Data
US 2015/0184891 A1 Jul. 2, 2015

(30) Foreign Application Priority Data
Jun. 7, 2012 (JP) .................................. 2012-130287

(51) Int. Cl.
*F24J 1/00* (2006.01)
*A61F 7/03* (2006.01)
*A61F 7/00* (2006.01)

(52) U.S. Cl.
CPC ................. *F24J 1/00* (2013.01); *A61F 7/034* (2013.01); *A61F 2007/0004* (2013.01)

(58) Field of Classification Search
CPC ..................................... A61F 7/034; F24J 1/00
(Continued)

(56) References Cited

U.S. PATENT DOCUMENTS 3,866,800 A * 2/1975 Schmitt .................. B65D 35/22
222/94
4,955,360 A * 9/1990 Ogawa ................... A45D 2/365
126/206

(Continued)

FOREIGN PATENT DOCUMENTS

CN 1068249 A 1/1993
CN 1491271 A 4/2004
(Continued)

OTHER PUBLICATIONS

Combined Chinese Office Action and Search Report dated Mar. 16, 2016 in Patent Application No. 201380029901.7 (with partial English language translation and English translation of categories of cited documents).

(Continued)

*Primary Examiner* — Avinash Savani
*Assistant Examiner* — Deepak Deean
(74) *Attorney, Agent, or Firm* — Oblon, McClelland, Maier & Neustadt, L.L.P.

(57) ABSTRACT

The present invention relates to a heating element (1) having an exothermic composition containing an oxidizable metal, a carbon component and water. Tri-alkali metal phosphate is contained in the heating element (1), and the content of water in the heating element (1) is equal to or larger than 50 parts by mass and equal to or smaller than 90 parts by mass for 100 parts by mass of the oxidizable metal, and the content of tri-alkali metal phosphate as a phosphate group is equal to or larger than 0.5 parts by mass and equal to or smaller than 1.1 parts by mass for 100 parts by mass of the oxidizable metal.

17 Claims, 7 Drawing Sheets

(58) Field of Classification Search
USPC .................................................. 126/263.01
See application file for complete search history.

(56) References Cited

U.S. PATENT DOCUMENTS

| | | | | |
|---|---|---|---|---|
| 5,046,479 | A | * | 9/1991 | Usui ....................... A61F 7/034 126/204 |
| 5,069,922 | A | | 12/1991 | Brotsky et al. |
| 5,143,739 | A | | 9/1992 | Bender et al. |
| 5,192,570 | A | | 3/1993 | Bender et al. |
| 5,262,186 | A | | 11/1993 | Bender et al. |
| 5,268,185 | A | | 12/1993 | Bender et al. |
| 5,283,073 | A | | 2/1994 | Bender et al. |
| 5,354,568 | A | | 10/1994 | Bender et al. |
| 5,477,847 | A | * | 12/1995 | Ueki .......................... F24J 1/00 126/263.01 |
| 5,512,309 | A | | 4/1996 | Bender et al. |
| 7,047,970 | B2 | * | 5/2006 | Umeda ................... A61F 7/034 128/203.26 |
| 7,611,767 | B2 | | 11/2009 | Usui et al. |
| 7,878,187 | B2 | | 2/2011 | York-Leung Wong |
| 8,357,189 | B2 | | 1/2013 | Ugajin et al. |
| 2004/0042965 | A1 | | 3/2004 | Usui et al. |
| 2004/0149732 | A1 | * | 8/2004 | Usui ....................... A61F 7/034 219/528 |
| 2004/0178384 | A1 | | 9/2004 | Usui |
| 2004/0217325 | A1 | | 11/2004 | Usui |
| 2006/0154006 | A1 | | 7/2006 | Usui et al. |
| 2007/0068508 | A1 | | 3/2007 | York-Leung Wong |
| 2009/0062890 | A1 | | 3/2009 | Ugajin et al. |
| 2009/0101867 | A1 | | 4/2009 | Ishikawa et al. |
| 2010/0241199 | A1 | * | 9/2010 | Hidaka .................. A61F 7/034 607/96 |
| 2013/0125837 | A1 | | 5/2013 | Ueno et al. |
| 2014/0345543 | A1 | | 11/2014 | Saita et al. |
| 2014/0373828 | A1 | | 12/2014 | Oka |

FOREIGN PATENT DOCUMENTS

| | | |
|---|---|---|
| CN | 1496395 A | 5/2004 |
| CN | 1518435 A | 8/2004 |
| CN | 1738883 A | 2/2006 |
| CN | 101146497 A | 3/2008 |
| CN | 101437476 A | 5/2009 |
| CN | 101820836 A | 9/2010 |
| JP | 11-239584 | 9/1999 |
| JP | 11-299818 | 11/1999 |
| JP | 2000-000260 | 1/2000 |
| JP | 2001-224622 A | 8/2001 |
| JP | 2003-633 A | 1/2003 |
| JP | 2003-336042 A | 11/2003 |
| JP | 2007-029131 | 2/2007 |
| JP | 2010-51690 A | 3/2010 |
| WO | WO 2011/158919 A1 | 12/2011 |

OTHER PUBLICATIONS

Combined Office Action and Search Report dated Jun. 16, 2016 in Russian Patent Application No. 2014152708 (with English translation and English translation of Categories of Cited Documents).

Combined Chinese Office Action and Search Report dated Jul. 30, 2015 in Patent Application No. 201380029901.7 (with Partial English Translation and English Translation of Category of Cited Documents).

International Search Report dated Aug. 13, 2013 in PCT/JP13/065821 Filed Jun. 7, 2013.

* cited by examiner

1

1A

HEATING ELEMENT AND HEATING IMPLEMENT CONTAINING THE SAME

TECHNICAL FIELD

The present invention relates to a heating element and a heating implement containing the heating element.

BACKGROUND OF THE INVENTION

A technology for housing an exothermic composition in a bag having air permeability, which is capable of producing heat by an oxidation reaction of an oxidizable metal, and producing heat in the presence of air, is known (Patent Documents 1 to 3).

Patent Document 1 describes an adhesive exothermic sheet for facial treatment, which includes an exothermic sheet composed of a flat parcel material having air permeability and a powdered exothermic composition included in the parcel material, and an adhesive layer.

Patent Document 2 describes a heating element including an exothermic composition that is capable of producing heat under the presence of air, and a flat parcel material composed of a base material and a coating material, in which the exothermic composition is contained, in which an aeration layer is deposited on one of or both of the above-described base material and the coating material on the side of a surface in contact with the exothermic composition, such that air flows in an interior through the aeration layer from an edge face of the aeration layer on the side of the circumference.

Patent Document 3 describes an air impermeable bag for a heating element that is capable of producing heat under the presence of air, in which an air-impermeable packaging material, which forms the air-impermeable bag for the heating element, is composed of at least a base material film coated with a metallic compound.

Patent Documents 1 and 2 also describe that a polyphosphate is contained in the exothermic composition as a pH adjuster.

Patent Document 3 describes the use of an alkali metal hydroxide and a weakly basic alkali metal salt as a hydrogen generation inhibitor.

RELATED DOCUMENTS

Patent Documents

[Patent Document 1]
Japanese Patent Publication No. H11-299818 (1999).
[Patent Document 2]
Japanese Patent Publication No. 2000-260.
[Patent Document 3]
Japanese Patent Publication No. H11-239584 (1999).

SUMMARY OF THE INVENTION

According to one aspect of the present invention, there is provided a heating element including an exothermic composition containing an oxidizable metal, a carbon component and water, wherein the heating element contains tri-alkali metal phosphate, wherein the content of the water in the heating element is equal to or larger than 50 parts by mass and equal to or smaller than 90 parts by mass for 100 parts by mass of the oxidizable metal, and wherein the content of the tri-alkali metal phosphate represented by an amount of a phosphate group ($PO_4^{3-}$) is equal to or larger than 0.5 parts by mass and equal to or smaller than 1.1 parts by mass for 100 parts by mass of the oxidizable metal, and a heating implement including thereof.

BRIEF DESCRIPTION OF THE DRAWINGS

The above and other features and advantages will be more apparent from the following description of certain preferred embodiments and accompanying drawings.

DETAILED DESCRIPTION OF THE INVENTION

None of technology focusing on antisepsis and antifungal treatment for an exothermic composition is described in the above-described Patent Documents 1 to 3.

The present inventors have focused their attention on a new challenge, in which an addition of water to an oxidizable metal and a carbon component during the manufacturing process may cause easy occurrence of fungi and mold in an exothermic composition in the subsequent process to require considerably complicated process control, and, the present inventors have found that a use of tri-alkali metal phosphate (($M_1^+)_3PO_4$: $M_1^+$ is an alkali metal ion.) can provide an antisepsis and antifungal ability to the exothermic composition, and that an addition of tri-alkali metal phosphate in the exothermic composition within a predetermined range of quantity results in a production of a heating element having favorable exothermic characteristics.

The present invention relates to a heating element, which is capable of providing an antisepsis and antifungal ability to an exothermic composition and exhibiting preferable exothermic characteristics.

According to the present invention, a heating element, which is capable of providing an antisepsis and antifungal ability to an exothermic composition and exhibiting preferable exothermic characteristics, can be presented.

Exemplary implementations according to the present invention will be described in detail as follows in reference to the annexed figures. In all figures, an identical numeral is assigned to an element commonly appearing in the figures, and the detailed description thereof will not be repeated.

Figure 1:
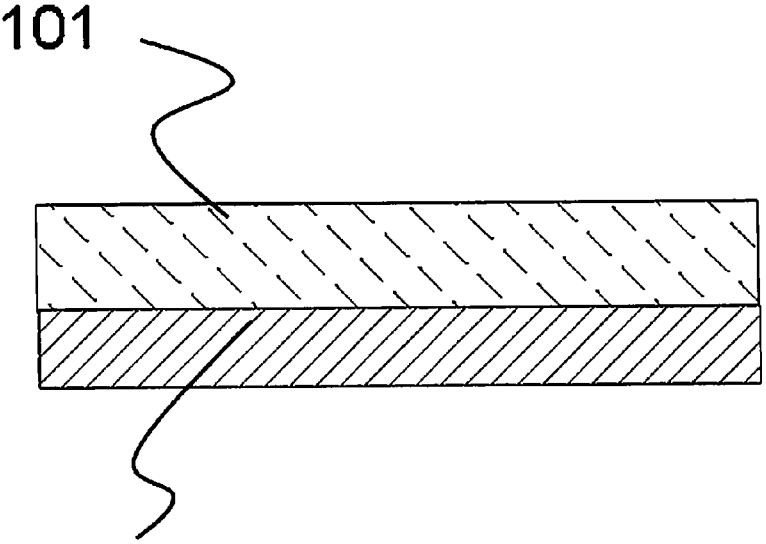
FIG. 1 is a cross-sectional view, schematically illustrating an example of a heating element according to an embodiment.

FIG. 1 illustrates a cross-sectional view of a heating element 1 according to the present embodiment. The heating element 1 includes an exothermic composition, which contains an oxidizable metal, a carbon component and water. The heating element 1 according to the present embodiment has an exothermic layer 101 and a base material layer 102 in layers.

The heating element 1 serves as providing sufficient heating effect with heat generated by oxidation reaction of the oxidizable metal, and is capable of exhibiting the performance of the exothermic temperature of equal to or higher than 40 degrees C. and equal to or lower than 70 degrees C. in the measurement based upon Japanese Industrial Standard (JIS) S4100 (1996 edition).

The oxidizable metal is a metal that is capable of releasing heat by an oxidation reaction, and typically includes, for example, powder or fiber of one, two or more selected from iron, aluminum, zinc, manganese, magnesium, and calcium. Among these, iron powder is preferable in view of a handle-ability, safety, manufacturing cost, storage stability and stability. Typical iron powder includes, for example, one, two or more selected from reduced iron powder and atomized iron powder.

When the oxidizable metal is a powdered state, the mean particle diameter of the powder is preferably equal to or larger than 10 µm, and more preferably is equal to or larger than 20 µm from the viewpoint that the oxidation reaction effectively occurs. Also, it is preferably equal to or smaller than 200 µm, and more preferably equal to or smaller than 150 µm. In addition, it is preferable that the mean particle diameter is from 20 to 150 µm.

Here, the particle diameter of the oxidizable metal means the maximum length in the configuration of the powder, and can be determined by the classification with sieves, dynamic light scattering, laser diffractometry or the like.

The content of oxidizable metal in the heating element 1 is preferably equal to or larger than 100 g/m$^2$ represented with the grammage, and is more preferably equal to or larger than 200 g/m$^2$. On the other hand, it is preferable to be equal to or lower than 3,000 g/m$^2$ and is more preferable to be equal to or lower than 1,500 g/m$^2$. Also, it is preferable to be from 100 to 3,000 g/m$^2$, and is more preferable to be from 200 to 1,500 g/m$^2$. This allows increasing the exothermic temperature of the heating element 1 to a desired temperature. Here, the content of the iron powder in the heating element 1 can be determined by an ash test pursuant to JIS P8128 (1995 edition), or by employing a thermogravimetry device. Another measurement may utilize a property of causing magnetization by applying an external magnetic field to carry out the quantification via the vibrating sample magnetometer test or the like.

The carbon component possesses a water-retention ability, oxygen supply ability and catalytic ability, and typically, for example, one, two or more selected from activated carbon, acetylene black, and black-lead may be available, and among these, activated carbon is preferably employed, in view of easy adsorption of oxygen in the wetted condition and in view of constant retention of water of the exothermic layer 101. More preferably, one, two or more of fine powdered material(s) or small granular material(s) selected from coconut shell carbon, wood powder carbon and peat may be employed. Among these, wood powder carbon is preferable, in view of providing enhanced exothermic efficiency of the heating element 1 and in view of allowing the maintenance of the content of water in the exothermic layer 101 and the base material layer 102 within the predetermined range.

It is preferable to employ the carbon component having the mean particle diameter of equal to or larger than 10 µm, not only from the standpoint of achieving the uniform mixing with the oxidizable metal but also from the standpoint of maintaining the content of the water contained in the base material layer 102 as being within a predetermined range, and it is more preferable to be equal to or larger than 12 µm, and on the other hand is preferable to equal to or smaller than 200 µm, and is preferable to equal to or smaller than 100 µm. It is also referable to employ the component having the mean particle diameter of from 10 to 200 µm, and is more preferable to employ the component having the mean particle diameter of from 12 to 100 µm.

Here, the particle diameter of the carbon component means the maximum length in the configuration of the powder, and can be determined by the dynamic light scattering, the laser diffractometry or the like.

While the carbon component having the form of the powder is preferably employed, those having the form other than the powder may alternatively be employed, and for example, those having the fibrous form may be employed.

The content of the carbon component may be preferably equal to or larger than 6 parts by mass for 100 parts by mass of the oxidizable metal, in view of not only providing enhanced exothermic efficiency of the heating element 1 but also in view of providing appropriate control for the content of water contained in the exothermic layer 101, and more preferably equal to or larger than 8 parts by mass, and on the other hand, is preferably equal to or smaller than 15 parts by mass and more preferably equal to or smaller than 13 parts by mass. It is also preferable to be from 6 to 15 parts by mass, and is more preferable to be from 8 to 13 parts by mass. This allows accumulating a sufficient amount of water required for sustaining the oxidation reaction in the heating element 101. Also, sufficient air permeability of the heating element 1 is ensured to provide enhanced exothermic efficiency due to sufficient amount of the oxygen supply. In addition, the heat capacity of the heating element 1 can be reduced as compared with the acquired amount of the heat generation, so that the temperature elevation due to the heat generation is increased and a preferable temperature elevation is obtainable.

The content of water in the entire heating element 1 is equal to or larger than 50 parts by mass and equal to or smaller than 90 parts by mass for 100 parts by mass of the oxidizable metal. It is preferably equal to or larger than 60 parts by mass, and is more preferably equal to or larger than 65 parts by mass. On the other hand, it is preferably equal to or lower than 85 parts by mass, and is more preferably equal to or lower than 80 parts by mass. Also, it is preferable to be from 60 to 85 parts by mass, and is more preferable to be from 65 to 80 parts by mass. This allows it to be used in combination with an oxidizable metal or the like so as to serve as a heat source. Also, this allows generation of a water vapor by the temperature elevation due to the production of heat. Also, when the exothermic layer 101 and the base material layer 102 is configured to be a layered structure, this allows providing enhanced ease of layering during the production process. It is sufficient that water is contained in at least the exothermic layer 101, and may also be contained in the base material layer 102.

The heating element 1 contains tri-alkali metal phosphate. This allows providing antibacterial and antifungal ability. Tri-alkali metal phosphate is a monophosphate represented by the chemical formula "$(M_1^+)_3 PO_4$ ($M_1^+$ is an alkali metal ion)". Alkali metal ion ($M_1^+$) contained in tri-alkali metal phosphate is preferably one, two or more type(s) selected from sodium ion ($Na^+$), potassium ion ($K^+$) and cesium ion ($Cs^+$), and is more preferably sodium ion or potassium ion.

The content of tri-alkali metal phosphate may be equal to or larger than 0.5 parts by mass as the phosphate group ($PO_4^{3-}$) for 100 parts by mass of the oxidizable metal, in view of providing antifungal and antisepsis abilities for the exothermic composition, and is more preferably equal to or larger than 0.6 parts by mass, and is even more preferably equal to or larger than 0.7 parts by mass. On the other hand, in view of obtaining enhanced exothermic temperature by achieving faster temperature rise, it is equal to or smaller than 1.1 parts by mass for 100 parts by mass of the oxidizable metal, and is more preferably equal to or smaller than 1 parts by mass, and is even more preferably equal to or lower than 0.9 parts by mass. Also, it is from 0.5 to 1.1 parts by mass for 100 parts by mass of the oxidizable metal, and is more preferably from 0.6 to 1 parts by mass, and is even more preferably from 0.7 to 0.9 parts by mass. This allows successfully producing heat with enhanced temperature rise when the heating element 1 is in contact with air.

In addition to the above, the content of tri-alkali metal phosphate may be calculated from the quantity of tri-alkali metal phosphate employed in the production of the heating element 1, or alternatively may be confirmed by measuring alkali metal ion with fluorescent X-ray spectrographic analysis after the heating element 1 is dried followed by being pelletized or being sintered to be velvety.

The heating element 1 can further contain an electrolyte as a reaction accelerator agent. The electrolyte is employed for sustaining oxidation reaction of the oxidizable metal. Also, the use of the electrolyte breaks an oxide film, which has been formed over the oxidizable metal by oxidation reaction, to promote the oxidation reaction. Typical electrolytes include one, two or more types selected from, for example, sulfates or chlorides of alkali metals or alkaline earth metals, ferrous chlorides and ferric chlorides. Among these, in view of providing improved electroconductivity, chemical stability and production cost, it is preferable to employ one, two or more types selected from various types of chlorides composed of chlorides of alkali metals and chlorides of alkaline earth metals.

Concerning chlorides of alkali metals ($M_2^+Cl^-$, alkali metal ions ($M_2^+$) contained in electrolyte is preferably one, two or more types selected from sodium ion ($Na^+$), potassium ion ($K^+$) rubidium ion ($Rb^+$) and cesium ion ($Cs^+$), and is more preferably sodium ion or potassium ion. In view of achieving uniform production of heat from the heating element 1, it is preferable to select a compound containing alkali metal ion ($M_2^+$) for the electrolyte, which is different from alkali metal ion contained in tri-alkali metal phosphate ($M_1^+$). Among these, sodium chloride and potassium chloride are preferable as chloride of alkali metal.

Also, it is preferable to employ calcium chloride and magnesium chloride as chloride of alkaline earth metal.

Mass ratio ($W_{K+}/(W_{K+}+W_{Na+})$) of a content ($W_{K+}$) of potassium ion ($K^+$) in the heating element 1 over summation ($W_{K+}+W_{Na+}$) of the content ($W_{K+}$) of potassium ion ($K^+$) and a content ($W_{Na+}$) of sodium ion ($Na^+$) in the heating element 1 is preferably equal to or higher than 0.1 in view of achieving uniform production of heat from the heating element 1, and is more preferably equal to or higher than 0.11, and is even more preferably equal to or higher than 0.12, and is even more preferably equal to or higher than 0.15. On the other hand, it is preferably equal to or lower than 0.6 in view of the production cost, and is more preferably equal to or lower than 0.5, and is even more preferably equal to or lower than 0.4. Also, it is preferable to be from 0.11 to 0.5, and is more preferably from 0.12 to 0.5, and is even more preferably from 0.15 to 0.4, and is even more preferably from 0.2 to 0.35.

On the contrary, the circumstance that ununiform production of heat from the heating element 1 causes fluctuations in the exothermic temperature of the heating element 1, which leads to avoiding thermal habituation of the human body and thus gives users the realization of warm sensation over a longer period of time, and in view of achieving this realization, mass ratio ($W_{K+}/(W_{K+}+W_{Na+})$) of a content ($W_{K+}$) of potassium ion ($K^+$) in the heating element 1 over summation ($W_{K+}+W_{Na+}$) of the content ($W_{K+}$) of potassium ion ($K^+$) and a content ($W_{Na+}$) of sodium ion ($Na^+$) in the heating element 1 is preferably lower than 0.11, and is more preferably lower than 0.1, and is even more preferably equal to or lower than 0.09, and is even more preferably equal to or lower than 0.07. On the other hand, in view of solubility of a salt, it is preferable to be equal to or higher than 0.001, and is more preferable to be equal to or higher than 0.005, and is even more preferable to be equal to or higher than 0.01. Also, it is preferable to be equal to or higher than 0.005 and lower than 0.11, and is more preferable to be equal to or higher than 0.001 and lower than 0.1, and is even more preferable to be from 0.005 to 0.09, and is even more preferable to be from 0.01 to 0.07.

Conventionally, a technology for causing fluctuation in the exothermic temperature by utilizing changes of air quantity entered in the exothermic member to inhibit physical habituation for temperature is known (Japanese Patent Publication No. 2006-204733), and this technology requires actions of the user. However, since no action of users is essential, it is capable of creating fluctuations in the exothermic temperature of the heating element 1 by ununiformly generating heat from the heating element 1 as described in the above, and therefore inhibition for the temperature habituation of the body can be achieved for broader situations of uses, and thus is even more preferable.

The heating element 1 may further contain a thickening agent. In such case, substances, which are capable of absorbing water to increase consistency or capable of providing thixotropic properties, may be mainly employed for the thickening agent, and a single substance selected from, or a mixture of two or more selected from the following may be used: polysaccharide-based thickening agents such as alginates, for example, sodium alginate, gum arabic, tragacanth gum, locust bean gum, guar gum, gum arabic, carrageenan, agar, xanthan gum and the like; starch-based thickening agents such as dextrin, pregelatinized starch, starch for processing and the like; cellulose derivative-based thickening agents such as carboxymethyl cellulose, ethyl acetate cellulose, hydroxyethyl cellulose, hydroxymethyl cellulose, hydroxypropyl cellulose and the like; metallic soap-based thickening agents such as stearate and the like; and mineral-based thickening agents such as bentonite and the like. Among these, the polysaccharide-based thickening agent is preferable, and its molecular weight is preferably equal to or higher than 1,000,000, and more preferably equal to or higher than 2,000,000, and on the other hand, is preferably equal to or lower than 50,000,000, and is more preferably equal to or lower than 40,000,000, and also, the preferable polysaccharide-based thickening agent have the molecular weight of preferably from 1,000,000 and 50,000,000, and more preferably from 2,000,000 to 40,000,000. Among these, in view of presenting improved production performance and salt resistance, xanthan gum is more preferable.

The content of the thickening agent in the heating element 1 is preferably equal to or larger than 0.05 parts by mass for 100 parts by mass of the oxidizable metal, and more preferably equal to or larger than 0.1 parts by mass, and on the other hand, is preferably equal to or smaller than 5 parts by mass, and is more preferably equal to or smaller than 4 parts by mass. Further, in view of providing a stable dispersion of the solid contents such as the oxidizable metal and the water absorption agent and providing thixotropic property to improve the coating performance for a base material sheet composing the base material layer 102, the content is preferably from 0.05 to 5 parts by mass, and is more preferably from 0.1 to 4 parts by mass.

The heating element 1 may additionally contain, as required, a surfactant, a drug, a flocculating agent, a coloring agent, a paper strengthening agent, a pH balancing agent, a bulking agent and the like. Further, the heating element 1 may contain one, two or more water absorption agent(s) selected from a fiber material, a water absorbent polymer and a water-absorbing powder, according to its conformation.

The heating element 1 may be composed of a powder-like, or a sheet-like exothermic composition. Among the exothermic sheet and the powders, it is preferable to employ the exothermic sheet, since the sheet can apply heat; heat can be uniformly evenly applied even if the wearer is in any position. The use of the exothermic sheet can easily provide uniform exothermic temperature distribution, as compared with the exothermic powder, and further can provide enhanced ability for supporting the oxidizable metal. Typical exothermic sheets include a product produced through a wet papermaking process, a product, in which an exothermic powder is interposed between fiber sheets such as papers, or a product produced by coating a base material sheet such as a paper with a dispersion of an exothermic powder and water or the like.

When the heating element 1 is an exothermic sheet, the base material layer 102 and the exothermic layer 101 may be in layers as shown by the figure, and the preferable configuration is a product, in which the exothermic layer 101 is layered over the base material layer 102. It is preferable that the exothermic layer 101 includes at least an oxidizable metal and a carbon component.

It is sufficient if the base material layer 102 can have the exothermic layer 101 layered thereon regardless of air permeability, and it is preferable to have air permeability. Air resistance of the base material layer 102 under the condition of absorbing water is preferably equal to or lower than 500 second/100 ml, and is more preferably equal to or lower than 300 second/100 ml, and on the other hand is preferably equal to or higher than 0 second/100 ml, and also is preferably 1 to 300 second/100 ml. The above described air resistances allow providing enhanced oxidation reaction of the oxidizable metal.

In the present specification, air resistance is a value measured according to JIS P 8117 (2009 Edition), and is defined as time required for air of 100 ml passing through an area of 6.45 cm$^2$ under the constant pressure. Air resistance can be measured with an Oken type air-permeability and smoothness tester or similar tester.

The base material layer 102 is preferably formed of a material having a water absorbability, and is more preferably formed of a water absorbent sheet. More specifically, the base material layer 102 may be formed of a sheet containing a fiber material such as, for example, a single-layer fiber sheet, and may alternatively be formed of a fiber sheet containing two or more layered sheets. The fiber sheet specifically includes papers or nonwoven fabrics produced of fiber materials, or products composed of layered papers and nonwoven fabrics. The sheet containing the fiber material may be more specifically a sheet material composed of a paper or a nonwoven fabric that is formed of one, two or more materials without water absorbability such as polyethylene fiber, polypropylene fiber, polyethylene sheet, polypropylene sheet and the like, on which a fiber material is layered or laminated, or a sheet material composed of produced-paper or nonwoven fabric that is formed of a fiber material such as a pulp fiber or a rayon fiber and another fiber material, which is layered thereon or mixed therein.

The base material layer 102 may further contain a water absorbent polymer. When the base material layer 102 contains the water absorbent polymer, the exemplary forms of the base material layer 102 may include: (i) the fiber material and the water absorbent polymer are uniformly mixed to form a single piece of sheet; (ii) the water absorbent polymer is disposed between same or different sheets containing the fiber material; and (iii) the water absorbent polymer is sprayed to form the sheet-like material. Among these, the preferable selection may be the conformation of (ii), since this allows easily controlling the water content of the exothermic layer 101. Meanwhile, the base material layer 102 of the conformation of (ii) may be produced by, for example, a method, in which the water absorbent polymer is uniformly sprayed over a sheet containing the fiber material, and 200 g/m$^2$ of water is sprayed thereon, and then the same or different type of a sheet containing the fiber material is further layered thereon and compression drying is carried out at 100± (plus or minus) 0.5 degrees C. and a pressure of 5 kg/cm$^2$ until the water content is reduced to equal to or lower than 5% by mass.

In the base material layer 102, typical water-absorbing polymers may include a hydrophilic polymer having the cross-link structure that is capable of absorbing and maintaining a significant amount of liquid that is 20 times of their own weight. Typical form of the water-absorbing polymer may be one, two or more selected from spherical form, massive form, grape cluster form and fibrous form. The particle diameter of the water absorbent polymer is preferably equal to or larger than 1 μm, and is more preferably equal to or larger than 10 μm, and on the other hand is preferably equal to or smaller than 1,000 μm, and is more preferably equal to or smaller than 500 μm. Also, it is preferably from 1 to 1,000 μm, and is more preferably from 10 to 500 μm.

In addition to the above, the particle diameter of the water-absorbing polymer particles may be determined by the dynamic light scattering, the laser diffractometry or the like.

Specific examples of the water absorbent polymer includes, for example, one, two or more selected from starches, cross-linked carboxymethyl celluloses, polyacrylic acids and their salts and polyacrylate graft polymers such as polymers or copolymers of acrylic acids or alkali metal salts of acrylic acids and the like. Among these, polyacrylic acids or their salts or polyacrylate graft polymers such as polymers or copolymers of acrylic acids or alkali metal salts of acrylic acids and the like may be preferably employed.

Proportion of the water absorbent polymer in the base material layer 102 is preferably equal to or higher than 10% by mass under the dried condition, and is more preferably equal to or higher than 20% by mass, and on the other hand is preferably equal to or lower than 70% by mass, and is more preferably equal to or lower than 65% by mass. Also, it is preferable to be from 10 to 70% by mass, and is more preferable to be from 20 to 65% by mass. This allows a rapid transfer of moisture to the base material layer 102, while anomalous heat production before the use can be prevented.

The base material layer 102 preferably has the grammage under the dried condition of equal to or larger than 20 g/m$^2$, more preferably equal to or larger than 35 g/m$^2$, and even more preferably equal to or larger than 50 g/m$^2$. On the other hand, it is preferably equal to or lower than 200 g/m$^2$, and more preferably equal to or lower than 150 g/m$^2$, and even more preferably equal to or lower than 140 g/m$^2$. Also, it is preferable to be from 20 to 200 g/m$^2$, and is more preferable to be from 35 to 150 g/m$^2$, and is even more preferable to be from 50 to 140 g/m$^2$.

The grammage of the water absorbent polymer contained in the base material layer 102 is preferably equal to or larger than 5 g/m$^2$ under the dried condition, and is more preferably equal to or larger than 10 g/m$^2$, and is even more preferably equal to or larger than 30 g/m$^2$. On the other hand, it is preferably equal to or smaller than 150 g/m$^2$, and is more preferably equal to or smaller than 100 g/m$^2$, and is even more preferably equal to or smaller than 90 g/m$^2$. Also, it is preferable to be from 5 to 150 g/m$^2$, is more preferable to be from 10 to 100 g/m$^2$, and is even more preferable to be from 30 to 90 g/m$^2$.

Figure 2:
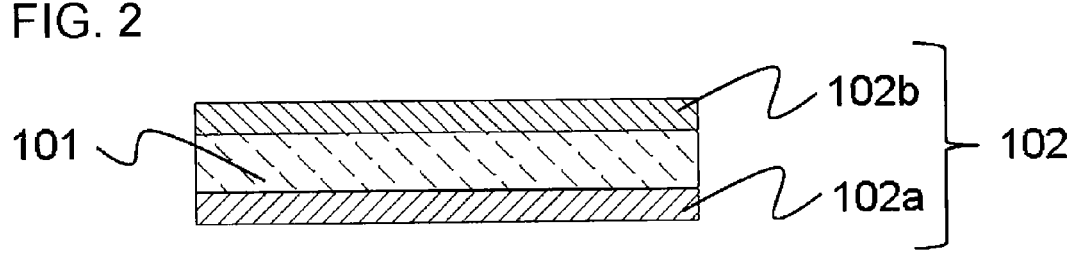
FIG. 2 is a cross-sectional view, schematically illustrating another example of a heating element according to an embodiment.

The base material layer 102 may be constituted to have the exothermic layer 101, which is formed on one side of the base material layer 102 as show in FIG. 1, or alternatively be constituted to have the exothermic layers 101, which are formed on both sides of the base material layer 102. In addition, as shown in FIG. 2, it may be formed of a first base material layer 102a and a second base material layer 102b. In such case, the heating element 1A may have a structure, in which the exothermic layer 101 is interposed between the first base material layer 102a and the second base material layer 102b, or so-called sandwich structure. The first base material layer 102a may be composed of a material that is same as, or that is different from, the material composing the second base material layer 102b. For example, if the first base material layer 102a is composed of multiple-layered material of two or more of fiber sheets, or of a material containing the fiber material and the water absorbent polymer and the second base material layer 102b is composed of a single fiber sheet, this constitution can provide enhanced oxidation reaction of the oxidizable metal, and therefore this constitution is preferable. In such case, the configuration in which the second base material layer 102b covers at least a portion of the exothermic layer 101 may be employed, and it is preferable to cover the entire surface of the exothermic layer 101.

Subsequently, a method for producing the heating element 1 will be described. Here, examples of the productions of the exothermic sheets of the heating element 1 for a sheet referred to as a fiber sheet, which contains the fiber, and for a sheet referred to as a coating sheet, which is produced by coating a paper and the like with the exothermic composition will be specifically described. When the heating element 1 is the fiber sheet, the production can be carried out by, for example, a wet papermaking process as described in Japanese Laid-Open Patent Publication No. 2003-102761, or an extrusion process employing a die coater. When the heating element 1 is the coating sheet, the production can be carried out by, for example, coating the base material with a slurry-form exothermic composition containing an oxidizable metal, a carbon component and water. While the production of the exothermic composition may be carried out by mixing all the above-described components at one time, an alternative way may be that an electrolyte is dissolved in a mixture that has been preliminarily produced by dissolving the thickening agent in water to prepare an aqueous solution, and then, a pre-mixture of the oxidizable metal and the carbon component is added therein. The constitution of the present invention allows acquiring antibacterial and antifungal effect during the manufacturing process of the fiber sheet and the coating sheet, which provides easy process control.

Figure 3:
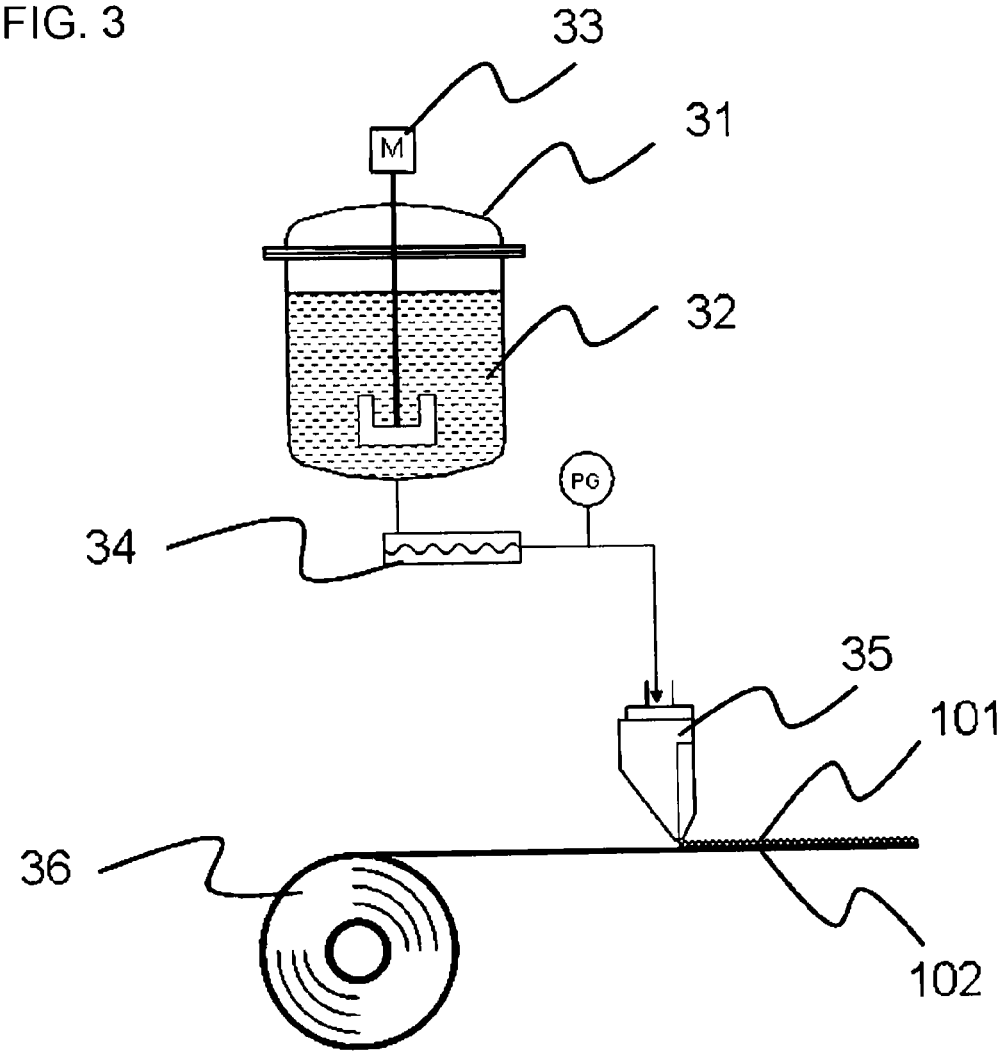
FIG. 3 is a schematic diagram for explaining an example of a method for producing a heating element according to an embodiment.

FIG. 3 is a diagram, which is useful in more specifically describing a method for producing the coating sheet. First of all, a slurry-form exothermic composition 32 containing an oxidizable metal, a carbon component, tri-alkali metal phosphate and water is prepared in a coating vessel 31. The slurry-form exothermic composition 32 is prepared with tri-alkali metal phosphate so as to achieve a pH of equal to or higher than 11. This allows the slurry-form exothermic composition 32 to have antibacterial and antifungal abilities.

The slurry-form exothermic composition 32 may be stirred by a stirrer 33 to more uniformly disperse insoluble components such as the oxidizable metal and the carbon component and the like in water. In addition to the above, the slurry-form exothermic composition 32 may be prepared by mixing all the above-described components at one time in the coating vessel 31, or an aqueous solution, which has been prepared by dissolving a thickening agent and tri-alkali metal phosphate in water to adjust the pH as being equal to or higher than 11, and an aqueous dispersion, which has been prepared by dispersing the carbon component in water and further dissolving tri-alkali metal phosphate to adjust the pH as being equal to or higher than 11, may be preliminarily prepared, and the aqueous solution, the aqueous dispersion and the oxidizable metal may be pre-mixed to be supplied in the coating vessel 31. This can provide an antibacterial and antifungal effect.

Then, the slurry-form exothermic composition 32 is pumped to a die head 35 by a pump 34. The pumped slurry-form exothermic composition 32 is pressurized and pushed by employing the die head 35 to be applied over a base material 36 such as a water absorbent sheet and the like. At this time, the coating grammage of the slurry-form exothermic composition 32 is preferably equal to or larger than 160 g/m$^2$, and is more preferably equal to or larger than 320, and on the other hand is preferably equal to or smaller than 4,800 g/m$^2$ and is more preferably equal to or smaller than 2,200 g/m$^2$. In addition, it is preferable to be from 160 to 4,800 g/m$^2$, and is more preferable to be from 320 to 2,200 g/m$^2$.

The electrolyte may be added in the coating vessel 31 to be contained in the slurry-form exothermic composition 32, or the slurry-form exothermic composition 32 may be applied and then a solution of the electrolyte dissolved in water may be added thereto via penetration, atomization or drip and the like, or the powder of the electrolyte may be sprayed. More specifically, while the mixing of the electrolyte serving as a reaction accelerator agent may be conducted simultaneously with the mixing of other components in the exothermic composition, an alternative way may be that the slurry-form exothermic composition is applied, and then a solution of the electrolyte dissolved in water is added thereto via penetration, atomization or drip and the like, or another alternative way may be to spray the powder of the electrolyte.

When the alkali metal ion ($M_1^+$) contained in tri-alkali metal phosphate is a potassium ion, an alkali metal ion ($M_2^+$) contained in the electrolyte may be preferably sodium ion, and when the alkali metal ion ($M_1^+$) contained in the tri-alkali metal phosphate is sodium ion, the alkali metal ion ($M_2^+$) contained in the electrolyte may be preferably a potassium ion. Among these, it is more preferable to select potassium ion for the alkali metal ion ($M_1^+$) contained in the tri-alkali metal phosphate and to select sodium ion for the alkali metal ion ($M_2^+$) contained in the electrolyte. In other words, the use of a combination of tripotassium phosphate and sodium chloride serving as the electrolyte is more preferable.

For example, when the exothermic layer containing tri-alkali metal phosphate is layered over the base material layer and then the electrolyte is added thereto, it is preferable in view of producing uniform heat from the heating element 1 that the alkali metal ion ($M_1^+$) contained in tri-alkali metal phosphate is different from the alkali metal ion ($M_2^+$) contained in the electrolyte. More specifically, more preferable approaches may be that the exothermic layer containing tripotassium phosphate is layered over the base material layer and then the electrolyte having sodium ion is added thereto, or that the exothermic layer containing tripotassium phosphate is layered over the base material layer and then the electrolyte having potassium ion is added thereto. Among these, the preferable approach is that the exothermic layer containing tripotassium phosphate is layered over the base material layer and then sodium chloride is added thereto.

Once the slurry of the above-described exothermic composition is applied over at least one surface of the base material, at least a portion of water contained in the exothermic composition is absorbed by the base material to form the exothermic layer 101 on the base material layer 102. More specifically, the exothermic layer 101 is composed of residual components that have not been absorbed by the base material layer 102. The exothermic layer 101 may be present on the base material layer 102, or alternatively, the lower section of the exothermic layer 101 may be leastwise partly buried in the base material layer 102. In addition, the exothermic layer 101 may be provided on one surface of the base material layer 102, or may be provided on both sides thereof. An example of providing the exothermic layer 101 on one side of the base material layer 102 is shown in FIG. 1.

While FIG. 3 illustrates the coating process via the die coating, the coating method is not limited thereto, and for example, a roll coating, screen printing, roll gravure, knife cording, curtain coater and the like may be applicable.

After the coating with the slurry-form exothermic composition 32, suction may be conducted from the surface where the exothermic layer 101 of the heating element 1 is not formed. This preferably allows providing enhanced integrity of the base material layer 102 and the exothermic layer 101. At this time, a suction pressure during the suctioning is preferably equal to or higher than 100 Pa and is more preferably equal to or higher than 500 Pa, and on the other hand is preferably equal to or lower than 10,000 Pa and is more preferably equal to or lower than 5,000 Pa. In addition, it is preferable to be from 100 to 10,000 Pa, and is more preferably from 500 to 5,000 Pa.

The suction pressure may be measured by mounting a manostar gauge in a box within a suction conveyer.

A continuous elongated workpiece including the exothermic layer 101 and the base material layer 102 is obtainable by the above described operations, and the obtainable workpiece is cut into pieces having desired sizes to form the heating element 1.

In addition to the above, a means for maintaining non-oxidation atmosphere may be employed as desired in the above-described method, in order to suppress the oxidation of the oxidizable metal during the production process.

Figure 4:
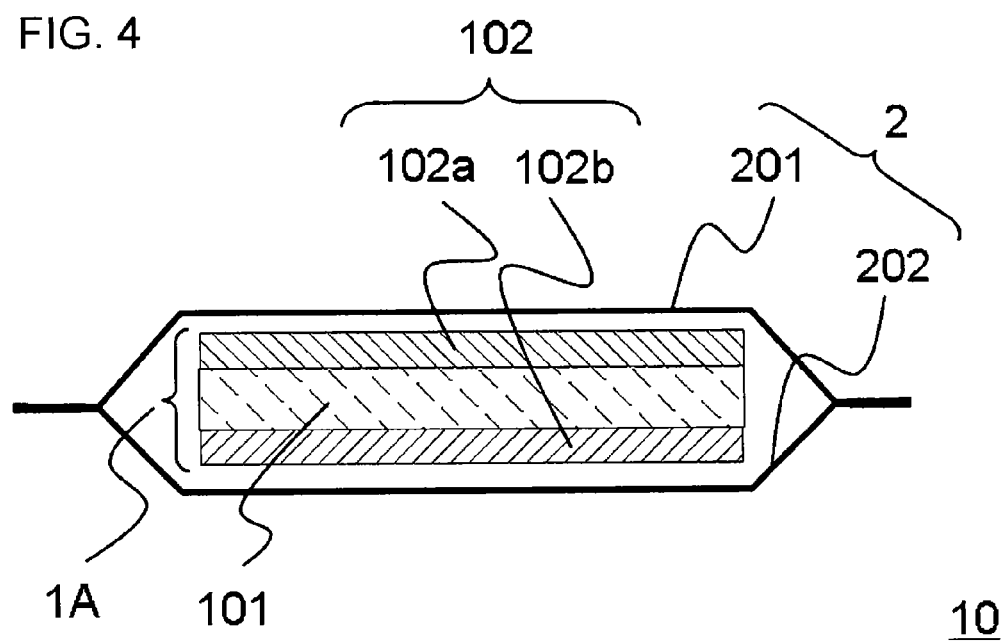
FIG. 4 is a cross-sectional view, schematically illustrating an example of a heating implement according to an embodiment.

FIG. 4 is a schematic cross-sectional view, showing an example of the heating implement including the heating element 1A shown in FIG. 2. As shown here, this heating implement 10 includes the heating element 1A having the sandwich structure, in which the exothermic layer 101 is interposed between the first base material layer 102a and the second base material layer 102b, and a bag 2, which leastwise partially has air permeability and is capable of housing the heating element 1A therein. The heating implement 10 may be a vapor heat generation equipment accompanied with the generation of water vapor, or so-called disposable handwarmer, which can produce heat substantially without the generation of water vapor.

More specifically, this heating implement 10 has a configuration, in which the heating element 1A having the exothermic layer 101 and the base material layer 102 is put in the bag 2 that leastwise partially has air permeability, and the circumference of the bag 2 is joined to provide a seal. Since the exothermic layer 101 is sandwiched between the first base material layer 102a and the second base material layer 102b, unwanted adhesion of the exothermic layer 101 to the bag 2 can be prevented.

The bag 2 is preferably composed of a first bag sheet 201 and a second bag sheet 202.

Each of the first bag sheet 201 and the second bag sheet 202 has a projecting region that projects from the outer circumference of the heating element 1A toward the outside thereof, and it is preferable the respective projecting regions thereof are joined. This joint is preferably a joint that is continuously airtight around the circumference. The bag 2 formed by the joint of the first bag sheet 201 with the second bag sheet 202 has a space in the interior thereof for housing the heating element 1A therein. The heating element 1A is housed in this space. The heating element 1A may be in the condition of being fixed to the bag 2, or in the condition of being not fixed thereto.

A portion of, or all of the first bag sheet 201 have air permeability. An air resistance (JIS P 8117 [2009 Edition]) of the first bag sheet 201 is preferably equal to or higher than 1,000 second/100 ml, and more preferably equal to or higher than 2,000 second/100 ml. On the other hand, the resistance of equal to or lower than 50,000 second/100 ml is preferable, equal to or lower than 35,000 second/100 ml is more preferable, and equal to or lower than 20,000 second/100 ml is even more preferable. Also, it is preferable to be from 1,000 to 50,000 second/100 ml, and is more preferable to be from 2,000 to 35,000 second/100 ml. It is preferable to employ, for example, a porous sheet of a synthetic resin having moisture permeability but having no water permeability for the first bag sheet 201 having such an air resistance. More specifically, a film manufactured by stretching polyethylene containing calcium carbonate may be employed. When such porous sheet is employed, various types of fiber sheets such as including one, two or more nonwoven fabric(s) selected from needle punch nonwoven fabric, air through nonwoven fabric and spunbond nonwoven fabric may be laminated over the outer surface of the porous sheet to provide an enhanced aesthetic effect of the first bag sheet 201. The first bag sheet 201 may be an aeration sheet, a portion of or the whole of which has air permeability, or may alternatively be non-aeration sheet having no air permeability, and may be preferably made of a sheet having higher air permeability than the second bag sheet 202 (that is, the sheet exhibiting lower air resistance).

The second bag sheet 202 may be an aeration sheet, a portion of or the whole of which has air permeability, or may alternatively be non-aeration sheet having no air permeability, and may be preferably made of a sheet having lower air permeability than the second bag sheet 201 (that is, the sheet exhibiting higher air resistance).

When the second bag sheet 202 is composed of a non-aeration sheet, a film manufactured with synthetic resin having a single layer or multiple layers may be employed, or various types of fiber sheets such as including one, two or more nonwoven fabric(s) selected from needle punch nonwoven fabric, air through nonwoven fabric and spunbond nonwoven fabric may be laminated over the outer surface of the aforementioned film manufactured with synthetic resin having a single layer or multiple layers to provide enhanced aesthetic effect of the first bag sheet 201. More specifically, a dual-layered film composed of a polyethylene film and a polyethylene terephthalate film, a laminate film composed of a polyethylene film and a nonwoven fabric, a laminate film composed of a polyethylene film and a pulp sheet and the like may be employed, and a laminate film composed of a polyethylene film and a pulp sheet is more preferable.

When the second bag sheet 202 is an aeration sheet, the bag sheet that is the same as the first bag sheet 201 may be employed, or a different bag sheet may alternatively be employed. When a different bag sheet is employed, it is preferable that the air permeability of the second bag sheet 202 is lower than that of the first bag sheet 201 and the air resistance of the second bag sheet 202 is equal to or higher than 65,000 second/100 ml, and is more preferably equal to or lower than 150,000 second/100 ml. In addition, the air resistance of the first bag sheet 201 may be more preferably equal to or higher than 2,000 second/100 ml and equal to or lower than 35,000 second/100 ml and the air resistance of the second bag sheet 202 may be more preferably equal to or higher than 65,000 second/100 ml and equal to or lower than 150,000 second/100 ml. Such air resistances can provide improved oxidation reaction of the oxidizable metal and in addition generate a larger quantity of water vapor from the side of the first bag sheet 201.

When the first base material layer 102a is produced by layering two or more fiber sheets or is configured to contain the fiber material and the water absorbent polymer and the second base material layer 102b is formed from one or more fiber sheet(s), it is preferable to enclose the first base material layer 102a on the side of the first bag sheet 201 and the second base material layer 102b on the side of the second bag sheet 202, and then the circumference sections are tightly sealed. Such configuration can provide improved oxidation reaction of the oxidizable metal and, in addition, enhanced generation of larger quantity of water vapor.

In addition to the above, in the case that the base material layer 102 is formed only on one side of the exothermic layer 101, for example, only the first base material layer 102a is employed without employing the second base material layer 102b, a direct contact of the exothermic layer 101 with the second bag sheet 202 may be possibly caused, and therefore it is preferable to employ a non-aeration sheet for the second bag sheet 202 in such case, in order to avoid the possibility of causing a change in the air permeability of the second bag sheet 202 due to adhesion of the exothermic layer 101.

A single heating element 1A may be housed in the bag 2, or those in a multiple-layered configuration layering a plurality of them may alternatively be housed therein.

Figure 5:
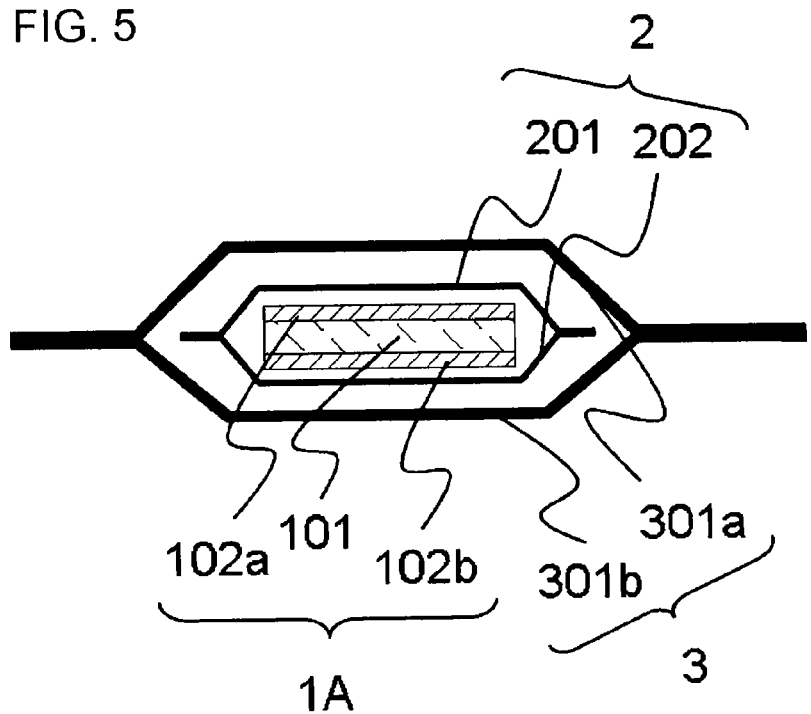
FIG. 5 is a cross-sectional view, schematically illustrating another example of a heating implement according to an embodiment.

Various types of fiber sheets may be laminated for the bag 2 in order to provide an enhanced aesthetic effect as described in the above, and may be housed in an exterior package 3 having air permeability to improve the aesthetic effect and the usability, as shown in FIG. 5. The exterior package 3 may preferably be composed of a first exterior sheet 301a and a second exterior sheet 301b, and may be configured such that the first exterior sheet 301a covers one surface of the bag 2 and the second exterior sheet 301b covers the other surface of the bag 2, and the first exterior sheet 301a is joined with the second exterior sheet 301b in the projecting region that projects from the outer circumference of the bag 2 toward the outside thereof, and it is preferable to form thereof by a tight seal. This allows forming a space in the interior of the exterior package 3 for housing the bag 2 therein, and the heating element 1A enclosed with the bag 2 can be housed in this space. The bag 2 may be in the condition of being fixed to the exterior package 3, or may be in a non-fixed condition.

The air permeability of the first exterior sheet 301a and the second exterior sheet 301b is preferably equal to or lower than 3,000 second/100 ml and is more preferably equal to or higher than 0 second/100 ml and equal to or lower than 100 second/100 ml, as long as it is higher than the air permeability of the first bag sheet 201. Such air resistance can provide improved oxidation reaction of the oxidizable metal and in addition generate a larger quantity of water vapor.

The types of the first and the second exterior sheets 301a and 301b composing the exterior package 3 are not limited to any specific type and typically are various types of fiber sheets including nonwoven fabrics and the like, as long as the material has air permeability, and for example, one, two or more selected from a needle punch nonwoven fabric, an air through nonwoven fabric and a spunbond nonwoven fabric may be employed.

The heating implement 50 may serve as a vapor heating implement, which is capable of generating water vapor by the oxidation reaction of the oxidizable metal, provided that the bag 2 has air permeability and the exterior package 3 also has air permeability.

The heating implement 50 may include an adhesive layer (not shown), which is formed by applying a cohesive agent over the outer surface of the exterior package 3, or for example, over the surface of the first exterior sheet 301a or the second exterior sheet 301b constituting the exterior package 3. The adhesive layer is utilized for fixing the heating implement 50 on a human skin or clothes or the like. Materials, which have been typically employed in the technical field, including a hot melt cohesive agent and the like, may be employed for the cohesive agent constituting the adhesive layer.

It is preferable that the heating implement 50 is housed in a tightly sealed condition in a package bag (not shown) having an oxygen barrier property until just before the use thereof.

The heating implement 50 may be directly applied to a human body, or may be mounted on clothes to be preferably employed for warming the human body. The applicable sites in the human body may include, for example, a shoulder, neck, eye, circumference of eye, waist, elbow, knee, thigh, leg, belly, lower abdominal region, hand, sole of foot and the like. This is also applicable to various types of articles other than the human body to be preferably employed for warming or heat retention. Further, when the heating implement 50 is a type of the heating implement for creating water vapor, water vapor may also be applied with a heat.

Figure 6:
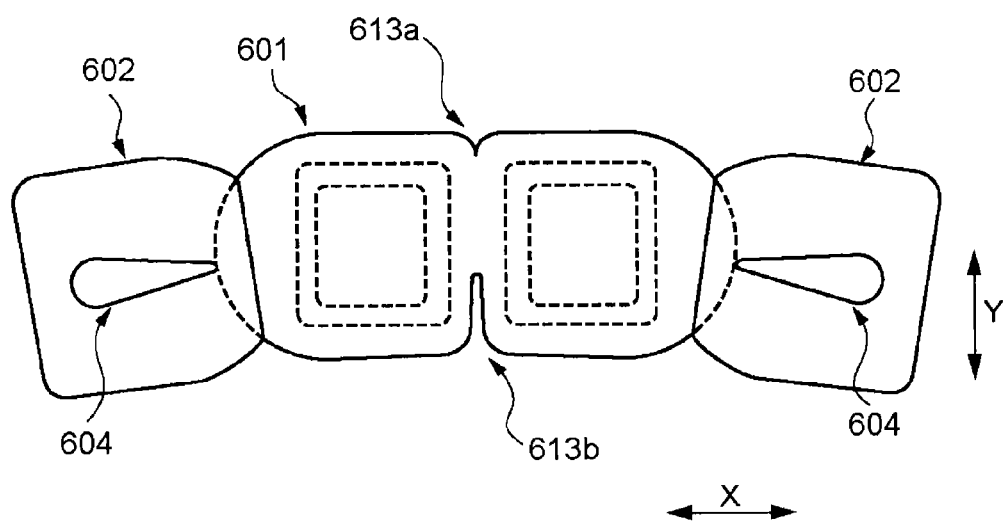
FIG. 6 is a plan view, schematically illustrating a specific example of a heating implement according to an embodiment.
Figure 7:
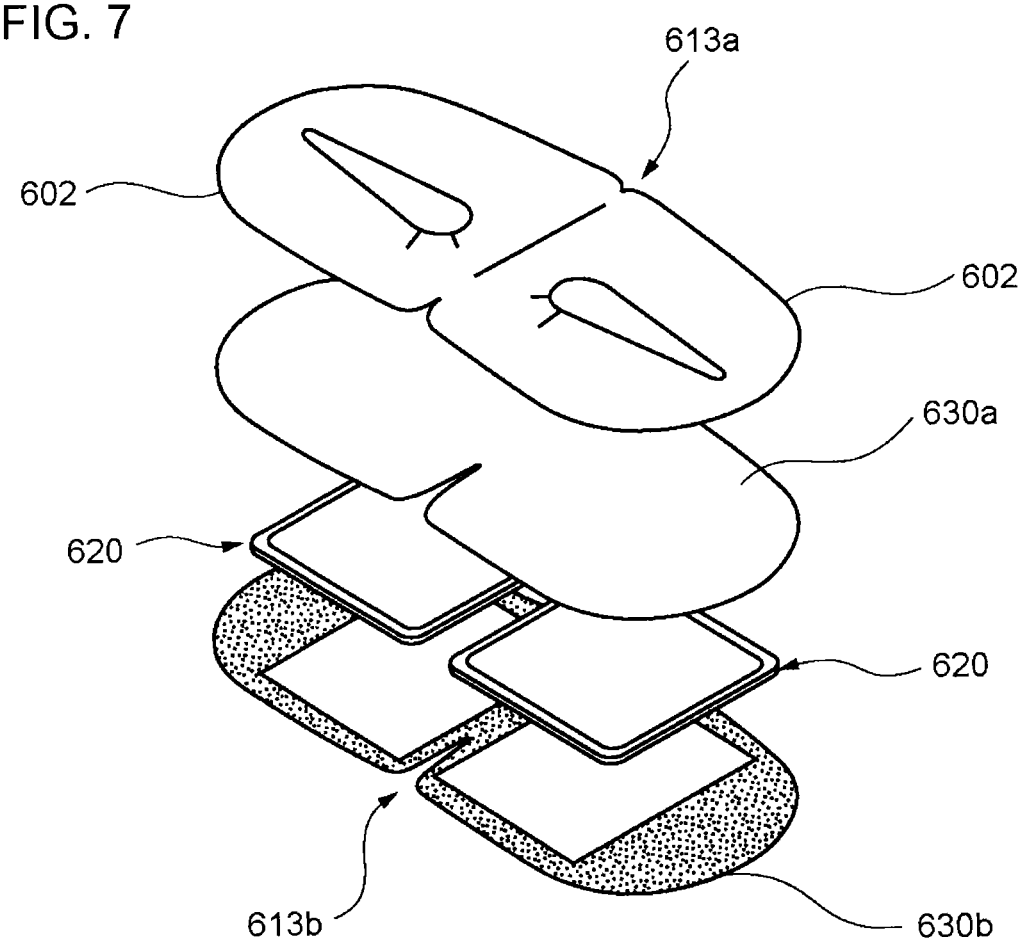
FIG. 7 is an exploded perspective view, schematically illustrating a specific example of a heating implement according to an embodiment.
Figure 8:
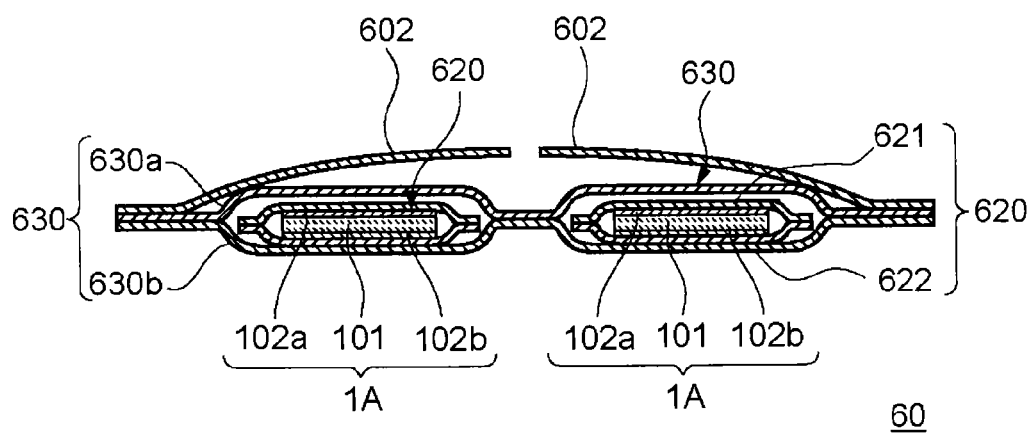
FIG. 8 is a cross-sectional view, schematically illustrating a specific example of a heating implement according to an embodiment.

The heating element employed in the present invention is preferable to be applicable to eyes, from the point of view of allowing the production of heat with enhanced rise in temperature. It is more preferable in this occasion to apply water vapor with a heat. FIGS. 6 to 8 illustrate an example of a vapor heating implement in the form of an eye mask. A vapor heating implement 60 may be employed so as to be in contact with human eyes and their circumferences to provide water vapor heated to a predetermined temperature (hereinafter referred to as "vapor heat") to the eye and their circumferences.

The vapor heating implement 60 includes a main body 601, and ear hooks 602 each being provided a hole 604, in which an ear is inserted. The main body 601 has an elongated shape having an elongating direction X and a width direction Y perpendicular to the elongating direction. The main body 601 has substantially an oval shape. The ear hooks 602 are employed as a pair, and each of the ear hooks 602 is mounted to each end in the elongating direction of the main body 601 (X direction). The vapor heating implement 60 is put on by hooking the respective ear hooks 602 on the ears of the wearer such that both eyes of the wearer are covered with the main body 601. Under such condition of fitting the equipment, the vapor heat generated from the vapor heating implement 60 comes in contact with the eyes of the wearer to relieve eyestrain, hyperemia and asthenopia, and also to achieve relaxation feel. Further, hypnagogic feel is also induced.

FIG. 7 shows an exploded perspective view of the vapor heating implement 60. In this diagram, the ear hooks 602 are disposed on the main body 601. FIG. 8 also shows a cross-sectional view of the vapor heating implement 60 along the X direction. The main body 601 of the vapor heating implement 60 includes the heating element 1A shown in FIG. 2, a bag 620 for housing the heating element 1A therein, and an exterior package 630 for further housing the bag 620.

The bag 620 is composed of a first bag sheet 621 positioned on the side close to a skin of a wearer and a second bag sheet 622 positioned on the side far from the skin of the wearer. The first bag sheet 621 may have similar constitution as the bag sheet 201 of the first in FIG. 4 and the second bag sheet 622 may have similar constitution as the second bag sheet 202 in FIG. 4, and the first bag sheet 621 may be an aeration sheet, a portion of or the whole of which has air permeability, and may be preferably made of a sheet having higher air permeability than the second bag sheet 622 (that is, the sheet exhibiting lower air resistance). More preferably, air resistance of the first bag sheet 621 may be equal to or higher than 2,000 second/100 ml and equal to or lower than 4,500 second/100 ml. Also, an aeration sheet having air resistance of equal to or higher than 65,000 second/100 ml and equal to or lower than 100,000 second/100 ml may be employed for the second bag sheet 622.

The exterior package 630 includes a first exterior sheet 630a positioned on the side closer to the skin of the wearer and a second exterior sheet 630b positioned on the side far from the skin of the wearer.

While similar materials as employed in the first and the second exterior sheets 301a and 301b may be employed for the first and the second exterior sheets 630a and 630b, respectively, the first exterior sheet 630a and the second exterior sheet 630b may preferably have the grammage of equal to or larger than 20 g/m$^2$, and on the other hand preferably equal to or smaller than 200 g/m$^2$ and more preferably equal to or smaller than 120 g/m$^2$, and also, it is preferable to have the grammage of from 20 to 200 g/m$^2$. The first exterior sheet 630a more preferably has a grammage of 20 to 120 g/m$^2$, in view of preventing from diaphanous appearance and in view of providing certain levels of heat retention, flexibility and thickness. Also, the second exterior sheet 630b more preferably has a grammage of 20 to 120 g/m$^2$, in view of preventing from diaphanous appearance and in view of providing certain levels of heat retention, flexibility and thickness. In view of releasing vapor and supplying oxygen to the heating element 1A, the air resistances of both the first exterior sheet 630a and the second exterior sheet 630b are preferably equal to or lower than 6,000 second/100 ml and more preferably equal to or lower than 1,000 second/100 ml. Water vapor evaporated from the base material layer 102 passes through the first bag sheet 621 and first exterior sheet 630a to reach the skin.

The first exterior sheet 630a and the second exterior sheet 630b have the equivalent shape, and are substantially oval. Then, the outer shapes of the first exterior sheet 630a and the second exterior sheet 630b form the outer shape of the main body 601. The first exterior sheet 630a is deposited over the second exterior sheet 630b and the circumference sections thereof are joined and those central sections in the X direction are also joined along the Y direction to form the exterior package 630 having two spaces in the interior thereof. Then, the heating elements 1A housed in the bags 620 are housed in the respective spaces, respectively. In order to join the first exterior sheet 630a to the second exterior sheet 630b, a hot melt adhesive agent, for example, may be employed. The bag 620 may be fixed to the exterior package 630 with an adhesive agent, heat sealing (not shown) or the like.

Formed in the exterior package 630 are substantially V-shaped notched sections 613a and 613b, which are disposed in positions of the central sections in the two longer sides extending toward the X direction, and have shapes of being notched inwardly along Y direction from the longer side. The notched sections 613a and 613b have different notched outlines. When the vapor heating implement 60 is worn, the notched section 613a is situated between the eyebrows of the wearer, or the vicinity thereof. When the vapor heating implement 60 is worn, the notched section 613b is situated on the nasal bridge of the wearer. Consequently, the notched section 613b may have a larger and deeper notched profile than the notched section 613a. Alternatively, at least one of the notched sections 613a and 613b shown in FIG. 6 may be a slit.

The ear hook 602 in the vapor heating implement 60 is, in the condition before use, disposed on the first exterior sheet 630a in the main body 601 as shown in FIG. 7 and FIG. 8. On the use of the vapor heating implement 60, the ear hook 602 is inverted toward the outside along the X direction to attain an opened condition as shown in FIG. 6. In the condition before use, or more specifically in the condition that the right and left ear hooks 602 are positioned on the main body 601, the profile formed by the right and left ear hooks 602 is substantially equivalent to the profile of the main body 601. The same material as that of the bag 620 may be employed for the ear hooks 602.

While the preferred embodiments of the present invention have been described in the above in reference to the annexed figures, it should be understood that the disclosures in the above are presented for the purpose of illustrating the present invention, and various modifications other than that described in the above are also available. For example, the heating element 1A of FIG. 2 may be replaced with the heating element 1 to constitute the heating implement as shown in FIGS. 4 and 5. Alternatively, the heating element 1A of FIG. 2 may be replaced with the heating element 1 of FIG. 1 to constitute the vapor heating implement as shown in FIGS. 6 to 8. Alternatively, the above-described heating elements 1 and 1A may also be employed for other types of heating implements having constitutions other than those shown in FIGS. 4 to 8, or may also be employed for other applications.

Concerning the embodiments as described in the above, the present invention will further disclose the following compositions, production methods or applications thereof.

<1> A heating element having an exothermic composition containing an oxidizable metal, a carbon component and, water, wherein the heating element contains tri-alkali metal phosphate, and wherein the content of water in the heating element is equal to or larger than 50 parts by mass and equal to or smaller than 90 parts by mass for 100 parts by mass of the oxidizable metal, and wherein the content of tri-alkali metal phosphate represented by an amount of phosphate group is equal to or larger than 0.5 parts by mass and equal to or smaller than 1.1 parts by mass for 100 parts by mass of the aforementioned oxidizable metal.

<2> The heating element as described in <1>, wherein the heating element contains an electrolyte, and the aforementioned electrolyte is preferably one, two or more of electrolyte(s) selected from the group consisting of a sulfate or chloride of alkali metal or alkaline earth metal, ferrous chloride and ferric chloride.

<3> The heating element as described in <2>, wherein the aforementioned electrolyte contains one, two or more selected from the group consisting of sodium chloride, potassium chloride, calcium chloride and magnesium chloride.

<4> The heating element as described in <2> or <3>, wherein the aforementioned electrolyte preferably contains second alkali metal ion, which is different from first alkali metal ion contained in the aforementioned tri-alkali metal phosphate.

<5> The heating element as described in <4>, wherein a combination of the aforementioned first alkali metal ion and the aforementioned second alkali metal ion is preferably sodium ion and potassium ion, and wherein mass ratio ($W_{K+}/(W_{K+}+W_{Na+})$) of the content of potassium ion ($W_{K+}$) in the heating element over summation ($W_{K+}+W_{Na+}$) of the aforementioned content of potassium ion ($W_{K+}$) and the content of sodium ion ($W_{Na+}$) in the heating element is preferably equal to or higher than 0.1, is more preferably equal to or higher than 0.12, and is even more preferably equal to or higher than 0.15, and on the other hand is preferably equal to or lower than 0.6, is more preferably equal to or lower than 0.5, and is even more preferably equal to or lower than 0.4.

<6> The heating element as described in <4>, wherein a combination of the aforementioned first alkali metal ion and the aforementioned second alkali metal ion is preferably sodium ion and potassium ion, and wherein mass ratio ($W_{K+}/(W_{K+}+W_{Na+})$) of the content of potassium ion ($W_{K+}$) in the heating element over summation ($W_{K+}+W_{Na+}$) of the aforementioned content of potassium ion ($W_{K+}$) and the content of sodium ion ($W_{Na+}$) in the heating element is preferably equal to or higher than 0.001, is more preferably equal to or higher than 0.005, and is even more preferably equal to or higher than 0.01, and on the other hand is preferably lower than 0.1, is more preferably equal to or lower than 0.09, and is even more preferably equal to or lower than 0.07.

<7> The heating element as described in any one of <3> to <6>, wherein the aforementioned electrolyte is preferably a chloride, and is more preferably sodium chloride or potassium chloride, and is further preferably sodium chloride.

<8> The heating element as described in any one of <1> to <7>, wherein the aforementioned oxidizable metal is preferably powder or fiber of one, two or more metal(s) selected from iron, aluminum, zinc, manganese, magnesium, and calcium; and is more preferably iron powder, and is further preferably one, two or more selected from reduced iron powder and atomized iron powder.

<9> The heating element as described in any one of <1> to <8>, wherein the content of the oxidizable metal in the aforementioned heating element is preferably equal to or larger than 100 g/m$^2$ represented by grammage, is more preferably equal to or larger than 200 g/m$^2$, and on the other hand is preferably equal to or lower than 3,000 g/m$^2$ and is more preferably equal to or lower than 1500 g/m$^2$.

<10> The heating element as described in any one of <1> to <9>, wherein the aforementioned carbon component is preferably one, two or more selected from activated carbon, acetylene black and black-lead.

<11> The heating element as described in <10>, wherein the aforementioned activated carbon is preferably one, two or more of fine powdered material(s) or granular material(s) selected from coconut shell carbon, wood powder carbon and peat.

<12> The heating element as described in any one of <1> to <11>, wherein mean particle diameter of the aforementioned carbon component measured by dynamic light scattering or laser diffractometry is preferably equal to or larger than 10 μm and is more preferably equal to or larger than 12 μm, and on the other hand is preferably equal to or smaller than 200 μm and is more preferably equal to or smaller than 100 μm.

<13> The heating element as described in any one of <1> to <12>, wherein the content of the aforementioned carbon component is preferably equal to or larger than 6 parts by mass for 100 parts by mass of the oxidizable metal, and is more preferably equal to or larger than 8 parts by mass, and on the other hand is preferably equal to or smaller than 15 parts by mass and is more preferably equal to or smaller than 13 parts by mass.

<14> The heating element as described in any one of <1> to <13>, wherein the content of the aforementioned water is preferably equal to or larger than 60 parts by mass for 100 parts by mass of the aforementioned oxidizable metal, and is more preferably equal to or larger than 65 parts by mass, and on the other hand is preferably equal to or smaller than 85 parts by mass and is more preferably equal to or smaller than 80 parts by mass.

<15> The heating element as described in any one of <1> to <14>, wherein the content of the aforementioned tri-alkali metal phosphate is preferably equal to or larger than 0.6 parts by mass as the phosphate group ($PO_4^{3-}$) for 100 parts by mass of the oxidizable metal, and is more preferably equal to or larger than 0.7 parts by mass, and on the other hand is preferably equal to or smaller than 1 parts by mass, and is more preferably equal to or smaller than 0.9 parts by mass.

<16> The heating element as described in any one of <1> to <15>, wherein the aforementioned tri-alkali metal phosphate is preferably trisodium phosphate or tripotassium phosphate, and is more preferably tripotassium phosphate.

<17> The heating element as described in any one of <1> to <16>, wherein the aforementioned heating element preferably further contains a thickening agent, and more preferably is a mixture of one, two or more selected from a polysaccharide-based thickening agent, a starch-based thickening agent, a cellulose derivative-based thickening agent, a metallic soap-based thickening agent and a mineral-based thickening agent, and is preferably a polysaccharide-based thickening agent having molecular weight is equal to or higher than 1,000,000 and is more preferably equal to or higher than 2,000,000 and on the other hand equal to or lower than 50,000,000 and is more preferably equal to or lower than 40,000,000, and is even more preferably xanthan gum.

<18> The heating element as described in <17>, wherein the content of the aforementioned thickening agent is preferably equal to or larger than 0.05 parts by mass for 100 parts by mass of the oxidizable metal, and is more preferably equal to or larger than 0.1 parts by mass, and on the other hand is preferably equal to or smaller than 5 parts by mass and is more preferably equal to or smaller than 4 parts by mass.

<19> The heating element as described in any one of <1> to <18>, wherein the aforementioned the heating element is preferably composed of the base material layer and the exothermic layer layered thereon.

<20> The heating element as described in <19>, wherein the aforementioned base material layer is preferably formed of a water absorbent sheet.

<21> The heating element as described in <20>, wherein the aforementioned water absorbent sheet is preferably configured by laminating one, two or more sheet(s) of a paper or a nonwoven fabric produced by a fiber material, or a fiber sheet composed of a lamination of a paper and a nonwoven fabric.

<22> The heating element as described in any one of <19> to <21>, wherein the aforementioned base material layer preferably contains a water absorbent polymer.

<23> The heating element as described in <22>, wherein the aforementioned base material layer is: (i) the fiber material and the water absorbent polymer are uniformly mixed to form a single piece of sheet; (ii) the water absorbent polymer is disposed between same or different sheets containing the fiber material; or (iii) the water absorbent polymer is sprayed to form the sheet-like material.

<24> The heating element as described in <22> or <23>, wherein particle diameter of the aforementioned water absorbent polymer is preferably equal to or larger than 1 μm and more preferably equal to or larger than 10 μm, and on the other hand is preferably equal to or smaller than 1,000 μm and more preferably equal to or smaller than 500 μm.

<25> The heating element as described in any one of <22> to <24>, wherein the aforementioned water absorbent polymer is preferably one, two or more selected from a starch, cross-linked carboxymethyl cellulose, polyacrylic acids and their salts and polyacrylate graft polymer such as a polymer or copolymer of acrylic acid or alkali metal acrylate.

<26> The heating element as described in any one of <22> to <25>, wherein the proportion of the water absorbent polymer the aforementioned base material layer under the dried condition is preferably equal to or higher than 10% by mass and is more preferably equal to or higher than 20% by mass, and on the other hand is preferably equal to or lower than 70% by mass and is more preferably equal to or lower than 65% by mass.

<27> The heating element as described in any one of <19> to <26>, wherein the grammage of the aforementioned base material layer is preferably equal to or higher than 20 $g/m^2$, is more preferably equal to or higher than 35 $g/m^2$, and is even more preferably equal to or higher than 50 $g/m^2$, and on the other hand is preferably equal to or lower than 200 $g/m^2$, is more preferably equal to or lower than 150 $g/m^2$, and is even more preferably equal to or lower than 140 $g/m^2$.

<28> The heating element as described in any one of <19> to <27>, wherein the aforementioned heating element contains a plurality of the aforementioned base material layers and the aforementioned exothermic layer is interposed between the aforementioned base material layers.

<29> The heating element as described in any one of <19> to <27>, wherein the aforementioned heating element contains a plurality of the aforementioned exothermic layers, and the aforementioned exothermic layers are formed on both sides of the aforementioned base material layer.

<30> A heating implement, containing: the heating element as described in any one of <1> to <29>; and a bag for housing the aforementioned the heating element therein, wherein a region having air permeability is provided in at least a portion of the aforementioned bag, and air resistance (JIS P 8117) of the aforementioned region having air permeability is equal to or higher than 1,000 second/100 ml and equal to or lower than 50,000 second/100 ml.

<31> The heating implement as described in <30>, wherein the aforementioned bag is formed by layering a first bag sheet and a second bag sheet and joining circumference section thereof, such that the heating element is housed in an interior of bag formed by the joint.

<32> The heating implement as described in <31>, wherein air resistance of the aforementioned first bag sheet is preferably equal to or higher than 2,000 second/100 ml and equal to or lower than 35,000 second/100 ml, and air resistance of the aforementioned second bag sheet is preferably equal to or higher than 5,000 second/100 ml and equal to or lower than 150,000 second/100 ml.

<33> The heating implement as described in <31> or <32>, wherein the air resistance of the aforementioned first bag sheet is lower than the air resistance of the aforementioned second bag sheet.

<34> The heating implement as described in any one of <30> to <33>, wherein water vapor is generated as the oxidizable metal is oxidized.

<35> A method for using a heating implement, in which the heating implement as described in any one of <30> to <34> is directly applied to a human body or is put on clothes, wherein the heating implement is preferably applied to eyes to apply water vapor with a heat, and wherein, in the case of the heating implement as described in <31> to <34>, the side of the first bag is applied to the human body or is put on the clothes.

<36> A method for producing the heating element as described in any one of <1> to <29> or the heating implement as described in any one of <30> to <34>, wherein an intermediate preformed product is made through a papermaking process with a raw composition containing at least an oxidizable metal, a carbon component water and tri-alkali metal phosphate, and then an electrolyte is contained in the intermediate preformed product.

<37> A method for producing the heating element as described in any one of <1> to <29> or the heating implement as described in any one of <30> to <34> by applying an exothermic composition containing at least an oxidizable metal, a carbon component, water and tri-alkali metal phosphate over a base material.

EXAMPLES

Examples 1 to 11 and Comparative Examples 1 and 2

A heating implement having a structure as show in FIG. 4 was produced as follows.

[Preparation of Slurry-Form Exothermic Composition]

An oxidizable metal, a carbon component, water, triphosphates, an electrolyte and a thickening agent were equipped according to relative proportions of components as shown in Table 1, and preparations were made by the following procedures. The thickening agent and the triphosphate were dissolved in water to prepare an aqueous solution, and on the other hand a pre-mixed powder of the oxidizable metal and the carbon component were prepared, and then the pre-mixed powder is added in the aqueous solution, and the mixture was stirred with a disc-turbine stirring blade at 150 rpm for 10 minutes to obtain a slurry-form exothermic composition. In addition to the above, types, product names and manufacturers for the oxidizable metal, the carbon component, water, triphosphates, the electrolyte and the thickening agent are as follows:

oxidizable metal: iron powder (commercially available from iron powder RKH, DOWA IP CREATION Co., Ltd.), mean particle diameter 45 μm;

carbon component: activated carbon (CARBORAFFIN, commercially available from Japan EnviroChemicals, Ltd.), mean particle diameter 40 μm;

water: tap water;

triphosphate A: tripotassium phosphate (commercially available from SHOWA KOSAN Co., Ltd.);

triphosphate B: trisodium phosphate (commercially available from SHOWA KOSAN Co., Ltd.);

electrolyte: Sodium chloride (Japanese Pharmacopoeia sodium chloride, commercially available from Otsuka Chemical Co., Ltd.); thickening agent: xanthan gum (echo gum BT, commercially available from DSP GOKYO FOOD & CHEMICAL Co., Ltd.), molecular weight 2,000,000.

[Preparation of Heating Element]

A polymer sheet, which was manufactured by layering: a paper made of wood pulp (grammage 20 g/m$^2$, commercially available from Inokami Co., Ltd.); a water absorbent polymer (crushed, mean particle diameter 300 μm, AQUALIC CA, commercially available from Nippon Shokubai Co., Ltd., grammage 50 g/m$^2$); and another paper made of wood pulp (grammage 30 g/m$^2$, commercially available from Inokami Co., Ltd.) to produce an integrated sheet (air resistance in the condition that an amount of water from 10 to 45% by mass of the maximum water absorption is absorbed: 2 second/100 ml), was employed as the first base material sheet, and a paper made of wood pulp (grammage 50 g/m$^2$, commercially available from Inokami Co., Ltd.) was employed as the second base material sheet. The polymer sheet to be employed as the first base material sheet was equipped, and 1.6 g each of the slurry-form exothermic composition, which had been prepared according to the above descriptions, was applied over a surface of the first base material sheet of 25 cm$^2$ (5 cm×5 cm, polyethylene sheet) to form a thickness of substantially 300 μm, and then the electrolyte was added thereto, and the applied surface was covered with the second base material sheet of 25 cm$^2$ (grammage 30 g/m$^2$, 5 cm×5 cm, polyethylene sheet) to obtain the heating element. In addition to the above, the quantity of 1.6 g employed in Example 1 was used as a reference for the quantity of the coating of the slurry-form exothermic composition, and the quantity of the coating was adjusted in other Examples and Comparative Examples so as to provide the same quantity of the iron powder as in Example 1.

[Preparation of Heating Implement]

Each of the heating elements of Examples 1 to 11 and Comparative Examples 1 and 2 was put in a bag having air permeability (6.5 cm×6.5 cm: air resistance of the first bag sheet: 2,500 second/100 ml, the second bag sheet was an air-impermeable sheet), so that the first base material sheet is disposed in the side of the first bag sheet and the second base material sheet is disposed in the side of the second bag sheet, and then the circumference sections were tightly sealed. Further, a peripheral section of a surface of an exterior bag (7.5 cm×7.5 cm) made of an air through nonwoven fabric (air resistance 0 second/100 ml, 30 g/m$^2$) was coated with a cohesive agent with an area of 1 cm wide×4 cm long at 100 g/m$^2$, and was further covered with a release paper, and the bag housing the heating element was put in the exterior bag and then the circumference section thereof was tightly sealed to obtain a heating implement. The heating implement was stored in an oxygen insulation bag until evaluation, as will be discussed later, was started.

[Evaluation]

1. Antisepsis and Antifungal

The tests were conducted according to the Preservatives-Effectiveness Tests, Japanese Pharmacopoeia, the 16th revision. One day after the start of the storage of the slurry-form exothermic composition at 25 degrees C., the result that the number of fungi was decreased as compared before the start of the storage was assigned as O and the result that the number of fungi was not decreased was assigned as x, and those results were shown in Table 1.

2. pH pH of the slurry-form exothermic composition was measured by employing a pH meter at 25 degrees.

3. Exothermic Characteristics

Measurements of heat generation were conducted with a measurement device based upon JIS S 4100 (1996 edition) by sticking the surface of the heating implement in the side of the first bag sheet on the measurement surface of the measurement device. More specifically, the maximum temperature (degrees C.), the rising of the temperature (time (minutes) taken from 35 degrees C. to 45 degrees C.), and the exothermic uniformity were evaluated. The "exothermic uniformity" was evaluated by measuring the temperatures in the center and four corners of the exothermic surface by using five thermoelectric couples, and when the difference between the maximum value and the minimum value of the measured temperature was within 2 degrees C., the result was "uniform", and when the difference was beyond 2 degrees C., this can be considered as being locally ununiform, and thus was "un-uniform".

TABLE 1

| | | | EXAMPLE 1 | EXAMPLE 2 | EXAMPLE 3 | EXAMPLE 4 | EXAMPLE 5 |
|---|---|---|---|---|---|---|---|
| HEATING ELEMENT FORMULATION (PARTS BY MASS) | OXIDIZABLE METAL | IRON POWDER | 100 | 100 | 100 | 100 | 100 |
| | CARBON COMPONENT | ACTIVATED CARBON | 8 | 8 | 8 | 11 | 11 |
| | WATER | TAP WATER | 62 | 62 | 62 | 62 | 72 |

TABLE 1-continued

|  |  |  |  |  |  |  |  |
|---|---|---|---|---|---|---|---|
|  | TERTIARY PHOSPHATE A | TRIPOTASSIUM PHOSPHATE | 1.12 | 2.4 | 1.12 | 2.4 | 1.8 |
|  | TERTIARY PHOSPHATE B | TRISODIUM PHOSPHATE |  |  |  |  |  |
|  | ELECTROLYTE | SODIUM CHLORIDE | 5 | 5 | 13 | 13 | 5 |
|  | THICKENING AGENT | XANTHAN GUM | 0.25 | 0.25 | 0.25 | 0.25 | 0.25 |
|  | PHOSPHATE GROUP QUANTITY (PARTS BY MASS) |  | 0.50 | 1.07 | 0.50 | 1.07 | 0.81 |
|  | $W_{K+}/(W_{K+} + W_{Na+})$ (MASS RATIO) |  | 0.24 | 0.4 | 0.11 | 0.21 | 0.34 |
| EVALUATIONS | ANTISEPTIC ACTIVITY/ANTIFUNGAL ACTIVITY |  | ○ | ○ | ○ | ○ | ○ |
|  | pH @ 25 DEGREES C. |  | ≥11 | ≥11 | ≥11 | ≥11 | ≥11 |
|  | EXOTHERMIC CHARACTERISTIC: MAXIMUM TEMPERATURE (A DEGREES CENTIGRADE) |  | 60-64 | 60-64 | 60-64 | 60-64 | 60-64 |
|  | EXOTHERMIC CHARACTERISTIC; RISING (35 DEGREES C. → 45 DEGREES C.) (min.) |  | 1-2.5 | 1-2.5 | 1-2.5 | 1-2.5 | 1-2.5 |
|  | EXOTHERMIC UNIFORMITY |  | UNIFORM | UNIFORM | UNIFORM | UNIFORM | UNIFORM |

|  |  |  | EXAMPLE 6 | EXAMPLE 7 | EXAMPLE 8 | EXAMPLE 9 | EXAMPLE 10 |
|---|---|---|---|---|---|---|---|
| HEATING ELEMENT FORMULATION (PARTS BY MASS) | OXIDIZABLE METAL | IRON POWDER | 100 | 100 | 100 | 100 | 100 |
|  | CARBON COMPONENT | ACTIVATED CARBON | 11 | 8 | 8 | 8 | 8 |
|  | WATER | TAP WATER | 72 | 62 | 62 | 90 | 50 |
|  | TERTIARY PHOSPHATE A | TRIPOTASSIUM PHOSPHATE | 1.8 |  | 0.5 | 1.12 | 1.12 |
|  | TERTIARY PHOSPHATE B | TRISODIUM PHOSPHATE |  | 1.5 | 1 |  |  |
|  | ELECTROLYTE | SODIUM CHLORIDE | 13 | 5 | 5 | 13 | 13 |
|  | THICKENING AGENT | XANTHAN GUM | 0.25 | 0.25 | 0.25 | 0.35 | 0.15 |
|  | PHOSPHATE GROUP QUANTITY (PARTS BY MASS) |  | 0.81 | 0.87 | 0.80 | 0.50 | 0.50 |
|  | $W_{K+}/(W_{K+} + W_{Na+})$ (MASS RATIO) |  | 0.16 | — | 0.10 | 0.11 | 0.11 |
| EVALUATIONS | ANTISEPTIC ACTIVITY/ANTIFUNGAL ACTIVITY |  | ○ | ○ | ○ | ○ | ○ |
|  | pH @ 25 DEGREES C. |  | ≥11 | ≥11 | ≥11 | ≥11 | ≥11 |
|  | EXOTHERMIC CHARACTERISTIC: MAXIMUM TEMPERATURE (A DEGREES CENTIGRADE) |  | 60-64 | 60-64 | 60-65 | 60-54 | 60-64 |
|  | EXOTHERMIC CHARACTERISTIC; RISING (35 DEGREES C. → 45 DEGREES C.) (min.) |  | 1-2.5 | 1-2.5 | 1-2.5 | 2-3 | 1-2.5 |
|  | EXOTHERMIC UNIFORMITY |  | UNIFORM | UN-UNIFORM | UN-UNIFORM | UNIFORM | UNIFORM |

|  |  |  | EXAMPLE 11 | COMPARATIVE EXAMPLE 1 | COMPARATIVE EXAMPLE 2 |
|---|---|---|---|---|---|
| HEATING ELEMENT FORMULATION (PARTS BY MASS) | OXIDIZABLE METAL | IRON POWDER | 100 | 100 | 100 |
|  | CARBON COMPONENT | ACTIVATED CARBON | 11 | 8 | 8 |
|  | WATER | TAP WATER | 72 | 62 | 62 |
|  | TERTIARY PHOSPHATE A | TRIPOTASSIUM PHOSPHATE | 2.8 | 0.8 | 6 |
|  | TERTIARY PHOSPHATE B | TRISODIUM PHOSPHATE |  |  |  |
|  | ELECTROLYTE | SODIUM CHLORIDE | 3 | 8 | 9 |
|  | THICKENING AGENT | XANTHAN GUM | 0.25 | 0 25 | 0.25 |
|  | PHOSPHATE GROUP QUANTITY (PARTS BY MASS) |  | 1.25 | 0.36 | 2.68 |
|  | $W_{K+}/(W_{K+} + W_{Na+})$ (MASS RATIO) |  | 0.57 | 0.12 | 0.48 |
| EVALUATIONS | ANTISEPTIC ACTIVITY/ANTIFUNGAL ACTIVITY |  | ○ | x | ○ |
|  | pH @ 25 DEGREES C. |  | ≥11 | ≤10.5 | ≥11 |
|  | EXOTHERMIC CHARACTERISTIC: MAXIMUM TEMPERATURE (A DEGREES CENTIGRADE) |  | 60-64 | 60-64 | 58≤ |
|  | EXOTHERMIC CHARACTERISTIC; RISING (35 DEGREES C. → 45 DEGREES C.) (min.) |  | 1-2.5 | 1-2.5 | >3.5 |
|  | EXOTHERMIC UNIFORMITY |  | UNIFORM | UNIFORM | UNIFORM |

While Comparative Example 1 failed to acquire antifungal and antisepsis ability since the content of triphosphate was smaller and pH of the slurry-form exothermic composition was less than 11, the slurry-form exothermic compositions of Examples 1 to 11, which contained certain amount of triphosphate so as to exhibit pH of equal to or higher than 11, acquired antifungal and antisepsis ability. While the heating element of Comparative Example 2, which contains excessive content of triphosphate, exhibited deterioration of exothermic characteristics, the heating elements of Examples 1 to 11, which contained a suitable amount of triphosphate, exhibited enhanced exothermic characteristics. Further, the heating elements of Examples 1 to 6 and 9 to 11 exhibited uniform exotherm without unevenness, as compared with the heating elements of Examples 7 and 8.

The present application claims priority on the basis of Japanese Patent Application No. 2012-130287, filed Jun. 7, 2012, the entire disclosures of which are hereby incorporated by reference.

The invention claimed is:

1. A heating element comprising: an exothermic composition having an oxidizable metal, a carbon component and water,
    wherein the heating element comprises tri-alkali metal phosphate,
    wherein the content of the water in the heating element is equal to or larger than 50 parts by mass and equal to or smaller than 90 parts by mass for 100 parts by mass of the oxidizable metal, and
    wherein the content of the tri-alkali metal phosphate represented by an amount of a phosphate group is equal to or larger than 0.5 parts by mass and equal to or smaller than 1.1 parts by mass for 100 parts by mass of the oxidizable metal,
    wherein the heating element comprises potassium ion and sodium ion, and
    wherein a mass ratio ($W_{K+}/(W_{K+}+W_{Na+})$) of the content of potassium ion ($W_{K+}$) in the heating element over a summation ($W_{K+}+W_{Na+}$) of the content of potassium ion ($W_{K+}$) and the content of sodium ion ($W_{Na+}$) in the heating element is equal to or higher than 0.1 and equal to or lower than 0.6.

2. The heating element according to claim 1, wherein the heating element further comprises at least one electrolyte selected from the group consisting of a sulfate or chloride of an alkali metal or alkaline earth metal, ferrous chloride, and ferric chloride.

3. The heating element according to claim 2, wherein the electrolyte is at least one electrolyte selected from the group consisting of sodium chloride, potassium chloride, calcium chloride and magnesium chloride.

4. The heating element according to claim 1, further comprising a thickening agent.

5. The heating element according to claim 4, wherein the thickening agent comprises at least one agent selected from the group consisting of a polysaccharide thickening agent, a starch thickening agent, a cellulose thickening agent, a metallic soap thickening agent, and a mineral thickening agent.

6. The heating element according to claim 1, wherein the heating element is in the form of a sheet and the content of the oxidizable metal in the heating element is from 100 to 3,000 $g/m^2$ represented by grammage.

7. The heating element according to claim 1, wherein the content of the carbon component is from 6 to 15 parts by mass for 100 parts by mass of the oxidizable metal.

8. The heating element according to claim 1, wherein the heating element comprises a base material layer and an exothermic layer in layers.

9. The heating element according to claim 8, wherein the base material layer is formed of a water absorbent sheet.

10. The heating element according to claim 9, wherein the water absorbent sheet comprises at least one layered sheet of a paper or a nonwoven fabric producible by a fiber material, or a fiber sheet having a paper and a nonwoven fabric in layers.

11. The heating element according to claim 8, wherein the base material layer further comprises a water absorbent polymer.

12. The heating element according to claim 8, comprising a plurality of the base material layers,
    wherein the exothermic layer is interposed between the base material layers.

13. The heating element according to claim 8, comprising a plurality of the exothermic layers,
    wherein the exothermic layers are formed on both sides of the base material layer.

14. A heating implement, comprising:
    the heating element according to claim 1; and
    a bag being capable of comprising the heating element,
    wherein a region having an air permeability is provided in at least a portion of the bag, and air resistance (JIS P 8117) of the region having an air permeability is equal to or higher than 1,000 second/100 ml and equal to or lower than 50,000 second/100 ml.

15. The heating implement according to claim 14, wherein the bag is provided by layering a first bag sheet and a second bag sheet and joining a circumference section thereof, such that the heating element is contained in an interior space of the bag formed by the joint.

16. The heating implement according to claim 15, wherein the first bag sheet has a higher air permeability as compared with the second bag sheet.

17. The heating implement according to claim 14, wherein water vapor is capable of being generated as the oxidizable metal is oxidized.

* * * * *